(12) United States Patent
Shinoda et al.

(10) Patent No.: US 10,279,369 B2
(45) Date of Patent: May 7, 2019

(54) PRINTING APPARATUS, THIN-FILM PRINTED BODY, AND METHOD OF MANUFACTURING THIN-FILM PRINTED BODY

(71) Applicant: Panasonic Intellectual Property Management Co., Ltd., Osaka (JP)

(72) Inventors: Masayo Shinoda, Tokyo (JP); Shuhei Nakatani, Osaka (JP); Kazuma Tsujita, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 394 days.

(21) Appl. No.: 15/063,697

(22) Filed: Mar. 8, 2016

(65) Prior Publication Data

US 2016/0288153 A1   Oct. 6, 2016

(30) Foreign Application Priority Data

Mar. 30, 2015   (JP) ................................. 2015-068356

(51) Int. Cl.
  *B05C 5/02*   (2006.01)
  *B41J 2/21*   (2006.01)
  (Continued)

(52) U.S. Cl.
  CPC ............ *B05C 5/0291* (2013.01); *A45D 44/00* (2013.01); *A45D 44/005* (2013.01); *A61K 8/0233* (2013.01); *A61Q 1/02* (2013.01); *B05C 5/027* (2013.01); *B05C 13/02* (2013.01); *B41J 2/2132* (2013.01); *B41J 2/2146* (2013.01); *B41J 3/407* (2013.01); *B41J 11/06* (2013.01); *A45D 2200/1027* (2013.01);
  (Continued)

(58) Field of Classification Search
  CPC ...... B41J 2/2132; B05C 5/0291; A45D 44/00; A45D 44/005
  USPC ...................................................... 347/2, 5, 9
  See application file for complete search history.

(56) References Cited

U.S. PATENT DOCUMENTS

2005/0253884 A1   11/2005  Matsumoto et al.
2006/0127580 A1   6/2006   Bae et al.
(Continued)

FOREIGN PATENT DOCUMENTS

CN   1695945 A    11/2005
JP   9-070988     3/1997
(Continued)

OTHER PUBLICATIONS

The Extended European Search Report dated Sep. 8, 2016 for the related European Patent Application No. 16159094.8.
(Continued)

*Primary Examiner* — An H Do
(74) *Attorney, Agent, or Firm* — Greenblum & Bernstein, P.L.C.

(57) ABSTRACT

Printing apparatus includes: a printer (thin-film carrier, conveyer, and droplet discharger) printing on a thin film by discharging, while shifting thin film in first direction, droplets containing a functional component from a plurality of positions differing from each other in second direction; and a print uniformity controller (print controller and position switcher) performing the printing for a plurality of times, by using the printer and changing position and/or orientation of thin film relative to the plurality of positions.

16 Claims, 11 Drawing Sheets

(51) Int. Cl.
*A61Q 1/02* (2006.01)
*B05C 13/02* (2006.01)
*A61K 8/02* (2006.01)
*B41J 3/407* (2006.01)
*B41J 11/06* (2006.01)
*A45D 44/00* (2006.01)
*B44C 1/10* (2006.01)

(52) U.S. Cl.
CPC .. *A45D 2200/1036* (2013.01); *A61K 2800/43* (2013.01); *B44C 1/105* (2013.01)

(56) References Cited

U.S. PATENT DOCUMENTS

| | | |
|---|---|---|
| 2008/0068432 A1 | 3/2008 | Sohn et al. |
| 2009/0128599 A1 | 5/2009 | Puigardeu et al. |
| 2012/0042799 A1 | 2/2012 | Kojima |
| 2012/0133694 A1 | 5/2012 | Oshige |
| 2016/0022014 A1 | 1/2016 | Ajiki et al. |
| 2016/0046120 A1 | 2/2016 | Sender Beleta et al. |

FOREIGN PATENT DOCUMENTS

| | | |
|---|---|---|
| JP | 2006-167704 | 6/2006 |
| JP | 2012-040813 A | 3/2012 |
| JP | 2012-126128 | 7/2012 |
| WO | 2014/147938 | 9/2014 |
| WO | 2014/161569 | 10/2014 |

OTHER PUBLICATIONS

English Translation of Chinese Search Report from State Intellectual Property Office (SIPO) of the People's Republic of China dated Dec. 25, 2018 for the related Chinese Patent Application No. 201610096185.X.

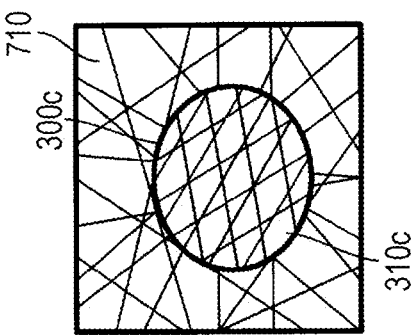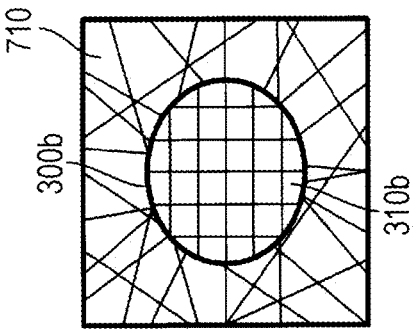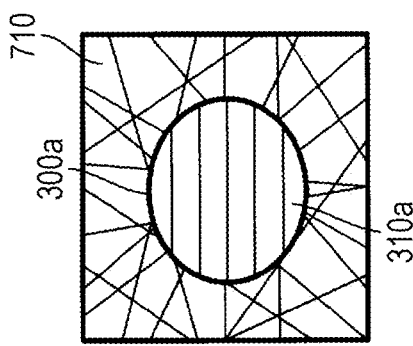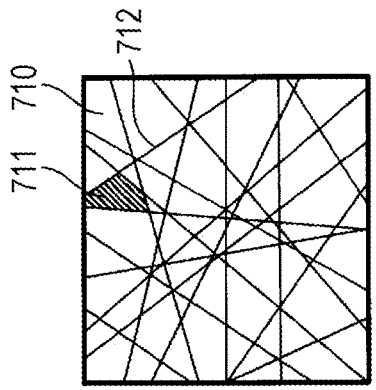

PRINTING APPARATUS, THIN-FILM PRINTED BODY, AND METHOD OF MANUFACTURING THIN-FILM PRINTED BODY

BACKGROUND

1. Technical Field

The present disclosure relates to a printing apparatus, a thin-film printed body, and a method of manufacturing the thin-film printed body.

2. Description of the Related Art

In recent years, a new scheme of makeup including printing a makeup material on a thin film and affixing the thin film on the skin is receiving attention. Hereinafter, a thin film on which a makeup material is printed is referred to as a "thin-film printed body".

In order to realize natural makeup, the image printed on the thin-film printed body is desirably well defined and shows less irregularities. Accordingly, it is contemplated to apply a technique relating to inkjet printing to the printing of a makeup material on a thin film (for example, see PTL 1).

According to the technique disclosed in PTL 1 (hereinafter referred to as the "conventional technique"), printing on paper is performed by discharging liquid from a plurality of nozzles of a head unit while shifting the head unit two-dimensionally along the paper. In the conventional technique, such printing is performed for a plurality of times while displacing the shifting route of the head unit.

According to the conventional technique, high-definition printing by inkjet printing can be performed. Further, for example, even when the discharge directions of the plurality of nozzles are not aligned and streak irregularities are formed in the printed image by the first print operation, since the positions where the ink droplets attach can be displaced in the second and the following print operations, the print irregularities can be effaced.

CITATION LIST

Patent Literature

PTL 1: Unexamined Japanese Patent Publication No. 2012-126128

However, when the head unit is shifted, stability in discharging the makeup material is impaired because of variations in the position of meniscus in the nozzles and vibrations of the piping. Then, the size or interval of droplets on the thin film becomes non-uniform. This may cause a loss of high-degree definition of printing, or an occurrence of noticeable print irregularities. That is, even when the conventional technique is applied to production of a thin-film printed body for makeup, natural makeup may not be realized.

Further, similarly to the above-described makeup material, droplets containing a variety of other functional components such as lotion or medications may also be printed on a thin film and the thin film may be affixed on the skin. In this case also, when there are print irregularities, the skin-care effect or the medication effect by the thin-film printed body may be largely lost.

SUMMARY

Thus, one non-limiting and exemplary embodiment of the present disclosure provides a printing apparatus capable of enhancing the effect of a thin-film printed body, the thin-film printed body, and a method of manufacturing the thin-film printed body.

In one general aspect, the techniques disclosed here feature:
A printing apparatus including a printer printing on a thin film by discharging, while shifting the thin film in a first direction, droplets containing a functional component from a plurality of positions differing from each other in a second direction; and a print uniformity controller that controls the printer to print such that position and/or orientation of the thin film is changed relative to the plurality of positions at each time of the printing.

These general and specific aspects may be implemented using a device, a system, a method, and a computer program, and any combination of devices, systems, methods, and computer programs.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

According to the present disclosure, the effect of a thin-film printed body can be enhanced.

BRIEF DESCRIPTION OF THE DRAWINGS

FIG. 6A shows exemplary relationship between skin texture and a print direction pattern according to the present exemplary embodiment;

FIG. 6B shows exemplary relationship between skin texture and a print direction pattern according to the present exemplary embodiment;

FIG. 6C shows exemplary relationship between skin texture and a print direction pattern according to the present exemplary embodiment;

FIG. 6D shows exemplary relationship between skin texture and a print direction pattern according to the present exemplary embodiment;

DETAILED DESCRIPTION

In the following, with reference to the drawings, a detailed description will be given of an exemplary embodiment of the present disclosure.

<Overview of Apparatus>

Firstly, a description will be given of the overview of a printing apparatus according to the present disclosure.

Figure 1:
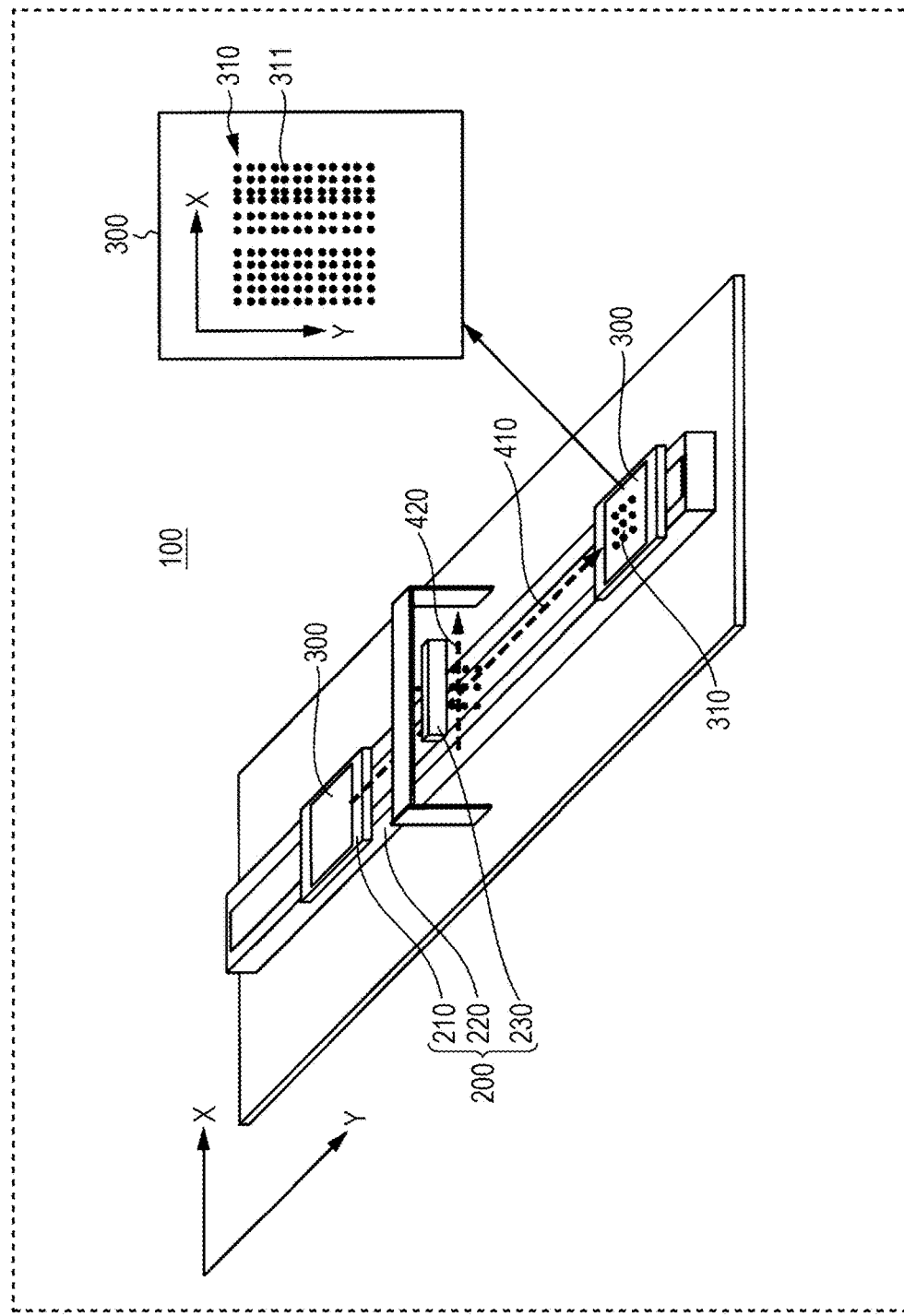
FIG. 1 shows an exemplary manner of printing by a printing apparatus according to the present disclosure.
Figure 2:
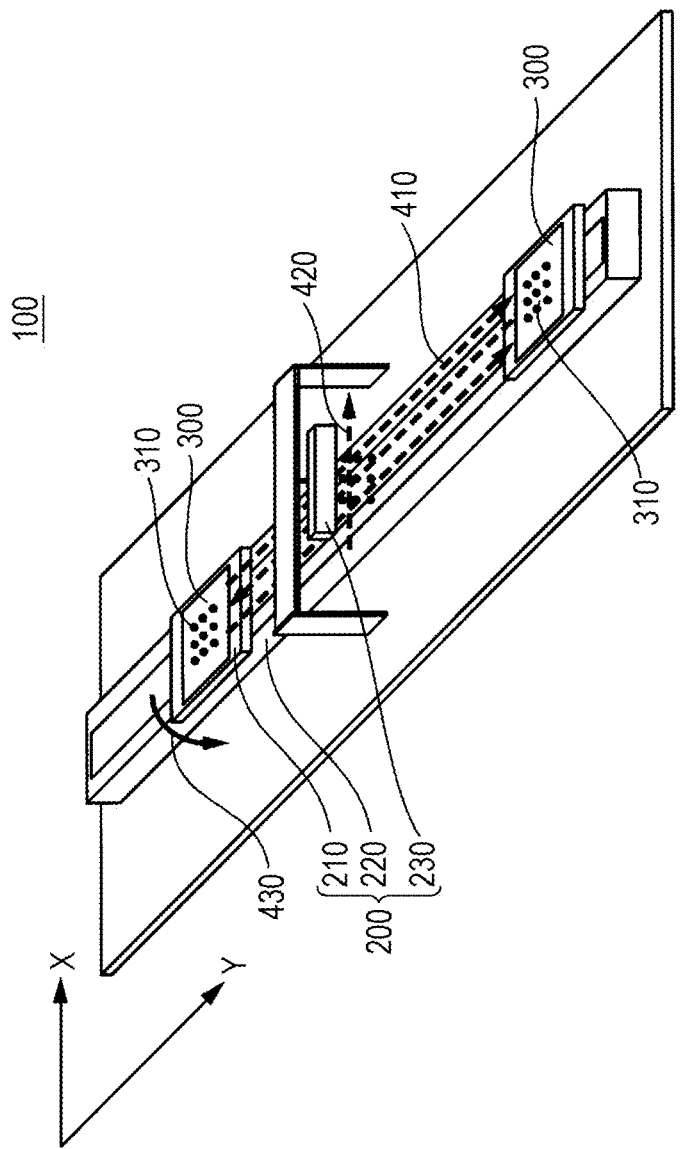
FIG. 2 shows an exemplary manner of printing by the printing apparatus according to the present exemplary embodiment.

FIGS. 1 and 2 each show an exemplary manner of printing by the printing apparatus according to the present disclosure.

As shown in FIG. 1, printing apparatus 100 includes, as printing mechanism 200 for printing a makeup material on thin film 300, stage 210, stage shifting mechanism 220, and makeup material discharging mechanism 230.

Stage 210 is a plate-like member, and on the upper surface of which thin film 300 having biocompatibility is placed. Stage shifting mechanism 220 shifts stage 210 in first direction 410 by a combination of a rail and a motor and the like. Note that, first direction 410 is substantially horizontal in the state where printing apparatus 100 is used.

Makeup material discharging mechanism 230 is provided halfway through the shifting route of stage 210 formed by stage shifting mechanism 220. Makeup material discharging mechanism 230 has a plurality of nozzles (not shown) disposed at regular intervals at different positions in second direction 420. Makeup material discharging mechanism 230 discharges a colored makeup material from the nozzles at the timing where thin film 300 placed on stage 210 passes immediately below. Note that, second direction 420 is substantially horizontal in the state where printing apparatus 100 is used, and perpendicular to the first direction 410.

That is, printing mechanism 200 discharges the makeup material from a plurality of positions different from each other in second direction 420 while shifting thin film 300 in first direction 410. Thus, printing mechanism 200 performs inkjet printing of the makeup material on thin film 300, to form image 310 on thin film 300. Note that, in the following description, as appropriate, first direction 410 is referred to as Y-axis direction or the main scanning direction, and second direction 410 is referred to as X-axis direction or the subordinate scanning direction.

Thin film 300 is a thin film being thin, having high color-transparency, and being capable of being tightly attached on the skin. Image 310 is, for example, a skin-color image having low transparency. By affixing such thin film 300 on a portion of the face desired to be concealed, such as spots, the makeup that effaces such a portion is realized.

In the case where stage 210 continuously or intermittently shifts at a constant speed in first direction 410 and makeup material discharging mechanism 230 discharges the makeup material at constant intervals, image 310 on thin film 300 is a matrix of a plurality of attached droplets (hereinafter referred to as the "dots") 311.

Desirably, the intervals of the plurality of dots 311 in first direction 410 and those in second direction 420 are constant. However, when the discharge speed or angle of the plurality of nozzles varies, the intervals of dots 311 vary.

Specifically, for example, variations in the repeated discharge of the nozzles cause speed variations of 0.08 m/s and angle variations of 3.1 mrad. At this time, the discharge variations among the plurality of nozzles cause speed variations of 0.71 m/s and angle variations of 23 mrad.

That is, the magnitude of variations in second direction 420 (X-axis direction) is about 10 times as great as the magnitude of variations in first direction 410 (Y-axis direction). Accordingly, with such inkjet printing, irregularities of streaks extending in first direction 410 (Y-axis direction) being the main scanning direction tend to occur (hereinafter referred to as the "streak irregularities").

Therefore, as shown in FIG. 2, after printing is once performed, printing apparatus 100 horizontally rotates 430 stage 210 relative to stage shifting mechanism 220 (that is, relative to the shifting direction of stage shifting mechanism 220) while returning stage 210 to the initial position. That is, printing apparatus 100 changes the orientation of stage 210 relative to the plurality of nozzles. Then, printing apparatus 100 again performs printing in the foregoing manner on thin film 300. Printing apparatus 100 alternately repeats for a plurality of times the printing on thin film 300 while shifting thin film 300 and the rotation of stage 210.

Thus, printing apparatus 100 effaces the streak irregularities by the second and following print operations, which are noticeable after the first print operation.

<Structure of Apparatus>

Next, a description will be given of a specific structure of printing apparatus 100.

Figure 3:
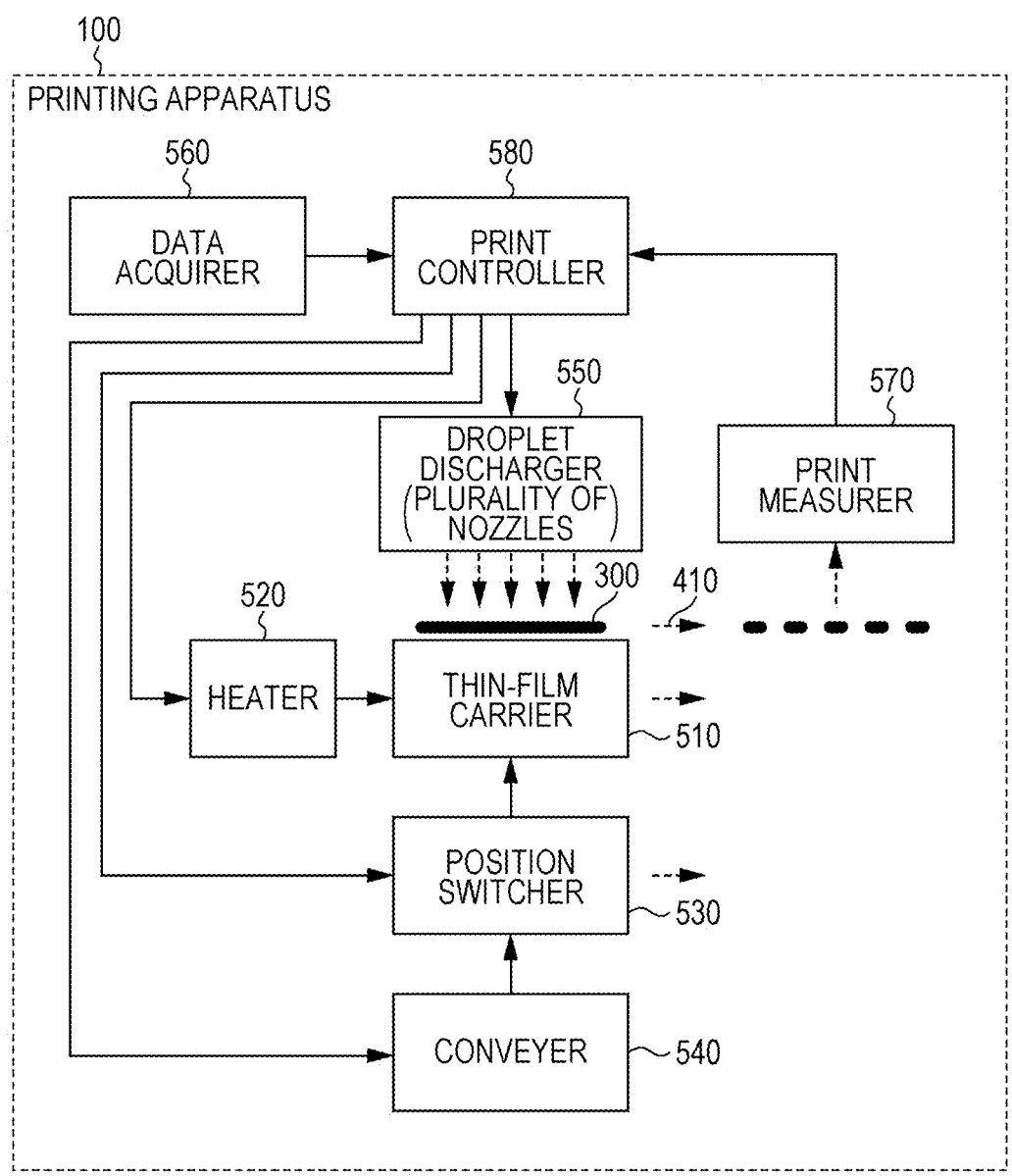
FIG. 3 shows an exemplary structure of the printing apparatus according to the present exemplary embodiment.

FIG. 3 is a block diagram showing an exemplary structure of the printing apparatus. Further, FIG. 4 is a schematic diagram showing an exemplary structure of printing apparatus 100 in association with a physical disposition.

Figure 4:
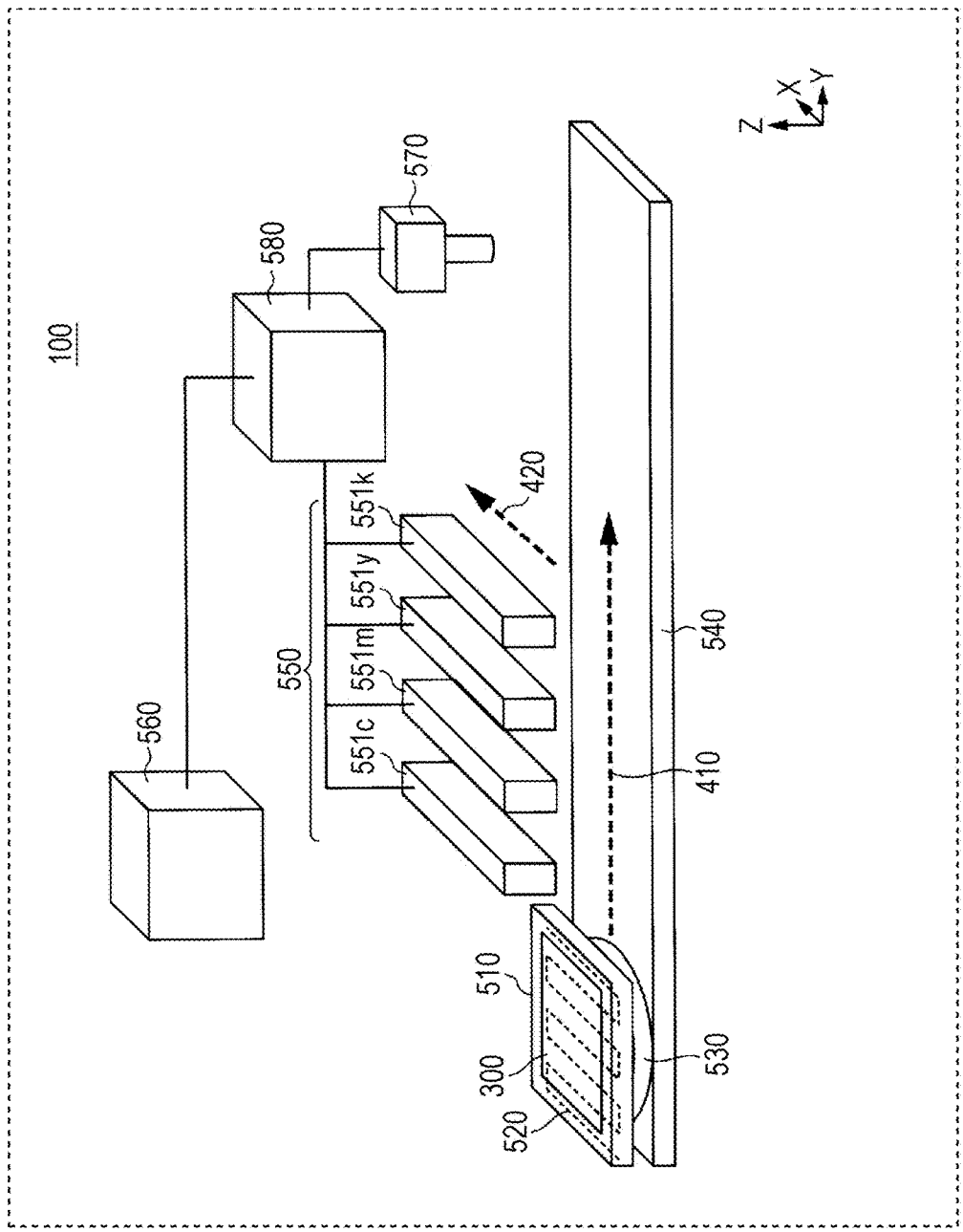
FIG. 4 shows an exemplary structure of the printing apparatus according to the present exemplary embodiment in association with a physical disposition.

As shown in FIGS. 3 and 4, printing apparatus 100 includes thin-film carrier 510, heater 520, position switcher 530, conveyer 540, droplet discharger 550, data acquirer 560, print measurer 570, and print controller 580.

Thin-film carrier 510 includes, for example, the above-described stage 210 (see FIGS. 1 and 2), and carries thin film 300. The detailed structure of thin film 300 will be described later.

Heater 520 heats thin film 300 carried by thin-film carrier 510. Heater 520 is, for example, an element arranged to form a plane inside stage 210. In this case, stage 210 is made of a material being heat-resistant and capable of transferring heat. Note that, heater 520 may be an apparatus which heats thin film 300 from the outside of stage 210, such as an infrared heater, a hot air blower heater or the like. Heater 520 heats such that, for example, thin film 300 carried by thin-film carrier 510 attains a prescribed temperature within a range of 20° C. to 50° C.

Position switcher 530 switches the orientation of thin-film carrier 510 in the horizontal direction relative to conveyer 540 whose description will be given later.

More specifically, position switcher 530 has a body portion supported by conveyer 540, a rotary table fixed to stage 210 pivotally supported on the upper side of the body portion, and a motor that rotates the rotary table relative to the body portion (each not shown). Then, position switcher 530 switches, by being controlled by print controller 580 whose description will be given later, the rotation angle of the rotary table relative to the body portion, thereby switching the rotation angle of the thin-film carrier 510 (and thin film 300 carried thereon) relative to conveyer 540. Details of the rotation of thin-film carrier 510 will be given later.

Conveyer 540 includes, for example, the above-described stage shifting mechanism 220 (see FIGS. 1 and 2), and connects to thin-film carrier 510 via position switcher 530, to shift thin-film carrier 510 in first direction 410 (Y-axis direction, see FIGS. 1 and 2) and the direction being reverse thereto.

More specifically, conveyer 540 supports the body portion of position switcher 530, and shifts, by being controlled by print controller 580 whose description will be given later, the body portion along first direction 410.

Droplet discharger 550 includes, for example, the above-described makeup material discharging mechanism 230 (see FIGS. 1 and 2), and discharges the makeup material from the plurality of nozzles (not shown) existing in second direction 420 (X-axis direction).

More specifically, droplet discharger 550 intermittently sprays, by being controlled by print controller 580 whose description will be given later, the makeup material from above thin film 300 shifting in first direction 410. Droplet discharger 550 has, for example, cyan discharger 551c, magenta discharger 551m, yellow discharger 551y, and black discharger 551k respectively discharging makeup materials of different colors.

Note that, a plurality of nozzles existing in second direction 420 (X-axis direction) do not necessarily mean a plurality of nozzles aligned on a straight line. That is, the plurality of nozzles are just required to be disposed at positions different from each other in second direction 420, and may be displaced from each other in first direction 410. Further, part of the plurality of nozzles may be disposed at an identical position in second direction 420.

Data acquirer 560 acquires print data representing the content of image (makeup image) 310 to be formed on thin film 300 (see FIGS. 1 and 2) and skin-color data representing the color of the skin of the user who is to put on makeup by affixing thin film 300 onto the face.

More specifically, data acquirer 560 communicates with a makeup simulator apparatus which determines the content of makeup, for example based on a captured image of the user's face, and receives the print data and the skin-color data from the apparatus. Note that, the color of the user's skin is, for example, the average value of the color of the entire face of the user, or the average value of the color of the skin around the region to which thin film 300 is affixed. Then, data acquirer 560 outputs the acquired print data and skin-color data to print controller 580.

Print measurer 570 includes, for example, a digital camera, and measures the color of thin film 300 having undergone printing, and outputs print state information representing the measured color of thin film 300 to print controller 580. Note that, when the color of the support body, whose description will be given later, disposed on the back side of thin film 300 is known, the color and transparency of image 310 can be measured from the apparent color of thin film 300.

Based on print data, print controller 580 controls shifting of thin-film carrier 510 by conveyer 540, and discharging of the makeup material by droplet discharger 550, to print image 310 on thin film 300.

Here, print controller 580 controls conveyer 540 such that thin-film carrier 510 passes immediately below droplet discharger 550 for a plurality of times, and controls droplet discharger 550 such that the makeup material is sprayed onto thin film 300 every time thin film 300 passes. That is, print controller 580 prints onto identical thin film 300 for a plurality of times. Further, print controller 580 controls position switcher 530 such that the orientation of thin-film carrier 510 is switched during such a plurality of print operations (horizontal rotation 430, see FIG. 2).

Further, print controller 580 controls heater 520 such that thin film 300 (or stage 210) attains a desired temperature at least while the orientation of thin-film carrier 510 is being switched. Then, print controller 580 determines whether or not to continue the printing based on a comparison between the color represented by the skin-color data and the color of thin film 300 represented by the print state information. Details of the structure of thin film 300 on which an image is printed (hereinafter referred to as the "thin-film printed body") will be described later.

Note that, among the constituent elements described above, for example, thin-film carrier 510, conveyer 540, and droplet discharger 550 can be regarded as a printer which prints on thin film 300 by discharging the makeup material from a plurality of positions differing from each other in the second direction while shifting thin film 300 in the first direction.

Further, among the constituent elements described above, for example, heater 520, position switcher 530, print measurer 570, and print controller 580 can be regarded as a print uniformity controller which performs the printing for a plurality of times using the printer while changing the orientation of the thin film relative to the plurality of positions.

Though not shown, printing apparatus 100 includes, for example, a CPU (Central Processing Unit), a storage medium such as ROM (Read Only Memory) storing a control program, a work memory such as RAM (Random Access Memory), and a communication circuit. In this case, the functions of the constituent elements described above are realized by the CPU executing the control program.

Though not shown and described, printing apparatus 100 may include a makeup material supplier supplying droplet discharger 550 with the makeup material, a thin-film supplier picking up thin film 300 and placing thin film 300 on thin-film carrier 510, and a thin-film ejector ejecting a thin-film printed body.

Printing apparatus 100 having such a structure is capable of printing while shifting thin film 300 and without shifting the nozzles or the head unit having the nozzles, and is further capable of changing the orientation of the thin film and performing the printing for a plurality of times.

Note that, in order to realize more natural makeup, desirably the printed image of the makeup material is high-definition. Accordingly, printing apparatus 100 desirably has the performance of about 600 dpi (dot per inch) or more, and the volume of droplets of the makeup material discharged from the nozzles at a single operation is desirably about 1 pL to 20 pL (picoliter).

Further, the material employed for thin film 300 must have not only biocompatibility but also a variety of characteristics such as thinness, color-transparency, flexibility, and elasticity. Therefore, as compared to a general printing medium such as paper, water absorbency may be reduced. In this case, droplets attached on the surface of thin film 300 tend to coagulate. This may invite irregularities in the printed image, and additionally the definition of the printed image may be reduced. Therefore, the discharged droplets are desirably sufficiently small. Further, thin film 300 is very thin and flexes when the makeup material is printed thereon.

The flexed thin film 300 and the nozzles may be brought into contact with each other, resulting in a damage of thin film 300. Therefore, printing apparatus 100 is desirably structured such that the gap between the nozzles and the surface of thin film 300 has a slightly great dimension of 1.5 mm to 3.0 mm.

<Structure of Thin Film>

Here, a description will be given of the structure of thin film 300.

Thin film 300 is a film having a thickness of about 100 nm to 1000 nm (nanometer), and being flexible and elastic. Therefore, at least when subjected to printing, thin film 300 is desirably removably affixed to a thicker and harder sheet-like support body. In the following, the member in which thin film 300 and the support body are integrated is referred to as the "stack-layer body".

Figure 5:
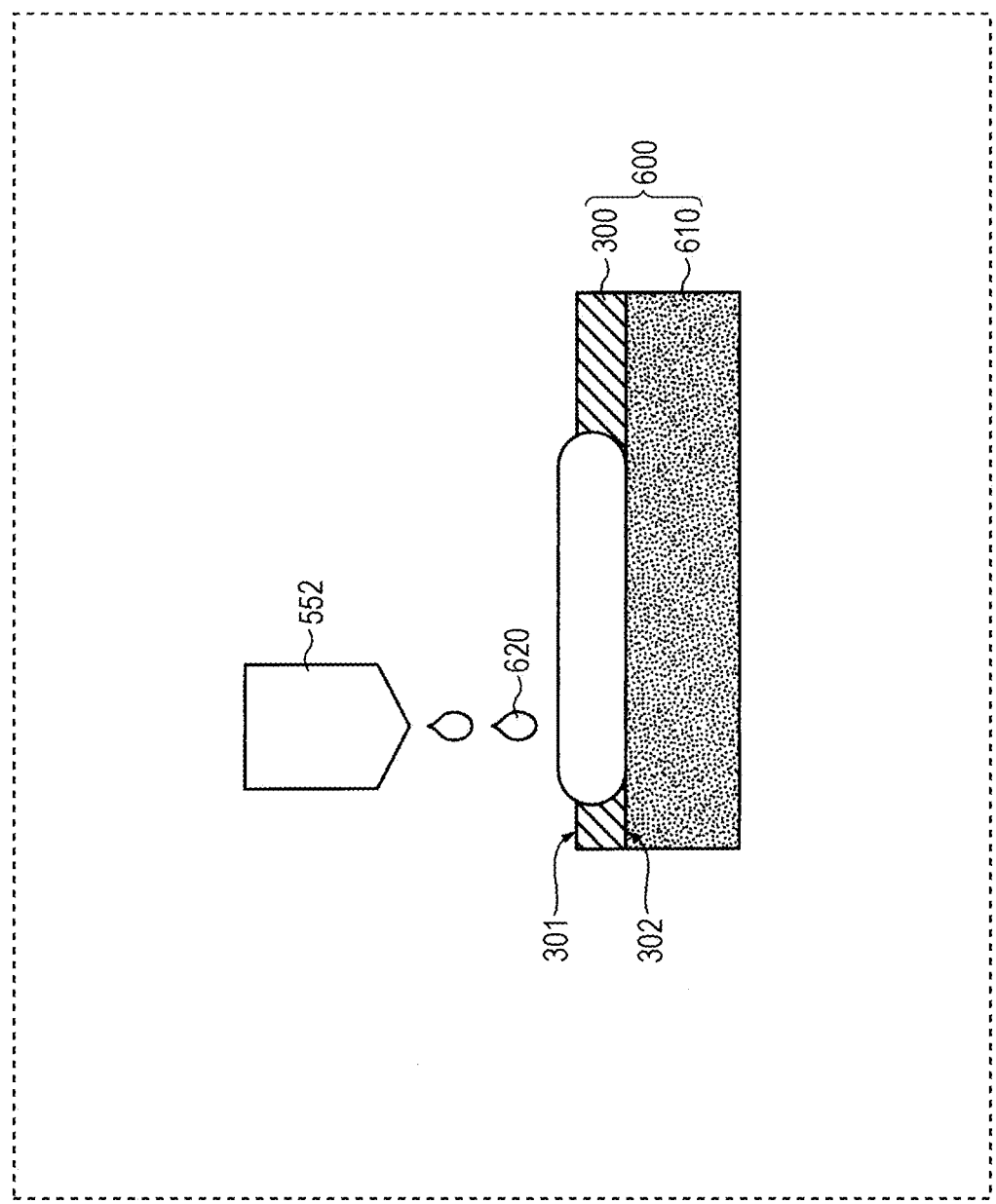
FIG. 5 shows an exemplary structure of a stack-layer body and an exemplary manner of printing according to the present exemplary embodiment.

FIG. 5 is a diagram showing an exemplary structure of the stack-layer body made up of thin film 300 and the support body, and an exemplary manner of printing onto thin film 300. Here, a description will be given of the case where the makeup material is a liquid mixture having biocompatibility and containing at least pigment and solvent such as water or glycerol.

As shown in FIG. 5, stack-layer body 600 is made up of support body 610 and thin film 300.

Support body 610 is made of a material exhibiting high water absorbency, for example, paper or a nanofiber sheet. Note that, in order to facilitate measurement of the color information including transparency of the image on the thin film, the color of support body 610 may be any color other than the color of the makeup material (black, blue or the like).

Thin film 300 is removably and tightly attached to support body 610, and has a thickness of 10 nm to 3000 nm, for example. Thin film 300 is made of a material having biocompatibility and permeability which allows, when makeup material 620 discharged from nozzles 552 is attached to front surface 301 not tightly attached to support body 610, makeup material 620 to permeate to back surface 302 tightly attached to support body 610. Such a material may be, for example, polyglycolic acid or polylactic acid.

In this manner, by stacking support body 610 exhibiting high water absorbency and thin film 300 exhibiting high permeability, fixation of pigment of the makeup material to thin film 300 is facilitated.

Note that, by the heating performed by heater 520 described above, the solvent of the makeup material attached to thin film 300 easily evaporates, and the time taken until fixation is reduced. As a result, in the case where printing is further performed onto a region having already subjected to printing, the possibility of coagulation of the already attached makeup material and the newly attached makeup material can be reduced.

<Rotation of Thin Film>

Next, a description will be given of rotation of thin-film carrier 510 (and thin film 300 carried thereon).

FIGS. 6A to 6D are diagrams showing exemplary relationship between the skin texture and various print direction patterns.

As shown in FIG. 6A, on human skin 710, triangular and rhombic mesh patterns (dermatoglyphic patterns) formed by cristae cutis 711 being relatively flat regions and sulci cutis 712 being linear grooves are evenly spread.

Directions of sulci cutis 712 are irregular. Accordingly, as shown in FIG. 6B, in the case where thin film 300a on which image 310a having streak irregularities aligned in one direction is affixed onto skin 710, the regularity of image 310a is noticeable and appears like wrinkles. As shown in FIG. 6C, with thin film 300b of image 310b having streak irregularities in two directions perpendicular to each other also, the regularity of image 310b may give the impression of being unnatural.

On the other hand, as shown in FIG. 6D, with thin film 300c of image 310c having streak irregularities in three directions not perpendicular to each other, the regularity is less likely to be recognized, and the impression approximates that of sulci cutis 712. Thus, the impression of being unnatural can be largely reduced.

Accordingly, position switcher 530 desirably switches the orientation of thin-film carrier 510 carrying thin film 300 by an angle other than a multiple of 90 degrees, and in a plurality of orientations being three or more. That is, position switcher 530 desirably rotates the orientation of thin-film carrier 510 twice or more by an angle other than a multiple of 90 degrees.

Figure 7:
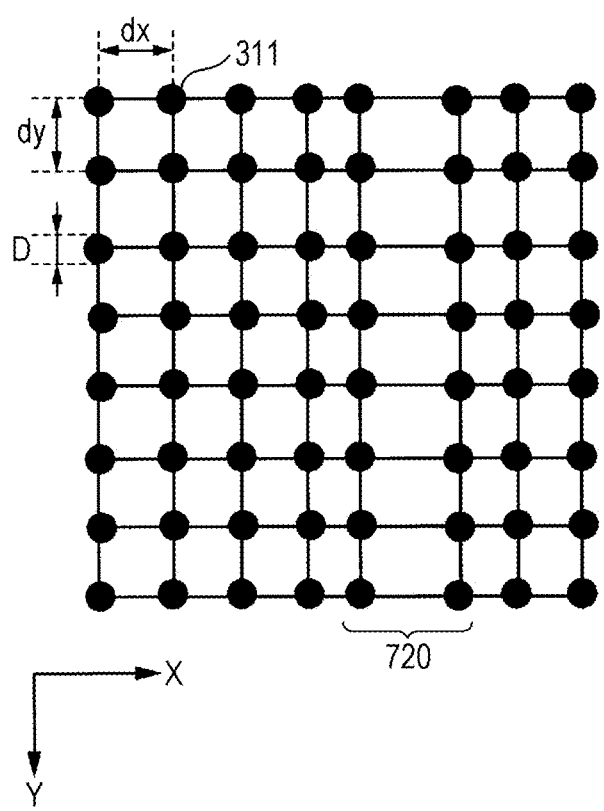
FIG. 7 shows an exemplary arrangement pattern of dots produced by a single print operation according to the present exemplary embodiment.

FIG. 7 is a diagram showing an exemplary arrangement pattern of dots 311 formed by a single print operation. Note that, the grid-like lines connecting dots 311 to each other are auxiliary lines and not printed lines.

Here, it is assumed that the set value of the interval in X-axis direction of dots 311 is dx, and the set value of the interval in Y-axis direction of dots 311 is dy. When the discharge speed or angle of a plurality of nozzles varies, a streak irregularity as represented by portion 720 in FIG. 7 is produced.

As described above, the plurality of print operations are desirably performed while thin film 300 is rotated twice or more by an angle other than a multiple of 90 degrees. Furthermore, it is desirable that dots 311 printed by the plurality of print operations do not overlap each other as much as possible. What rotation angle can avoid overlap of dots 311 as much as possible depends on intervals dx, dy and diameter D of dots 311.

For example, it is assumed that diameter D of dots 311 is 20 μm to 30 μm (micrometer) and intervals dx, dy of dots 311 are each 42.3 μm (corresponding to 600 dpi). In this case, when thin film 300 is rotated by angle θ which satisfies 42.3 μm×tan θ=30 μm, overlap of dots 311 after the rotation can be suppressed. Accordingly, position switcher 530 desirably rotates thin-film carrier 510 within a range of angle θ=35.3° to 54.7°.

Note that, when diameter D is 20 μm, rotation angle θ may be 25.3° to 60°. Further, in the case where micro droplets are printed at a resolution higher than 600 dpi, a further smaller angle θ may be employed.

Figure 8:
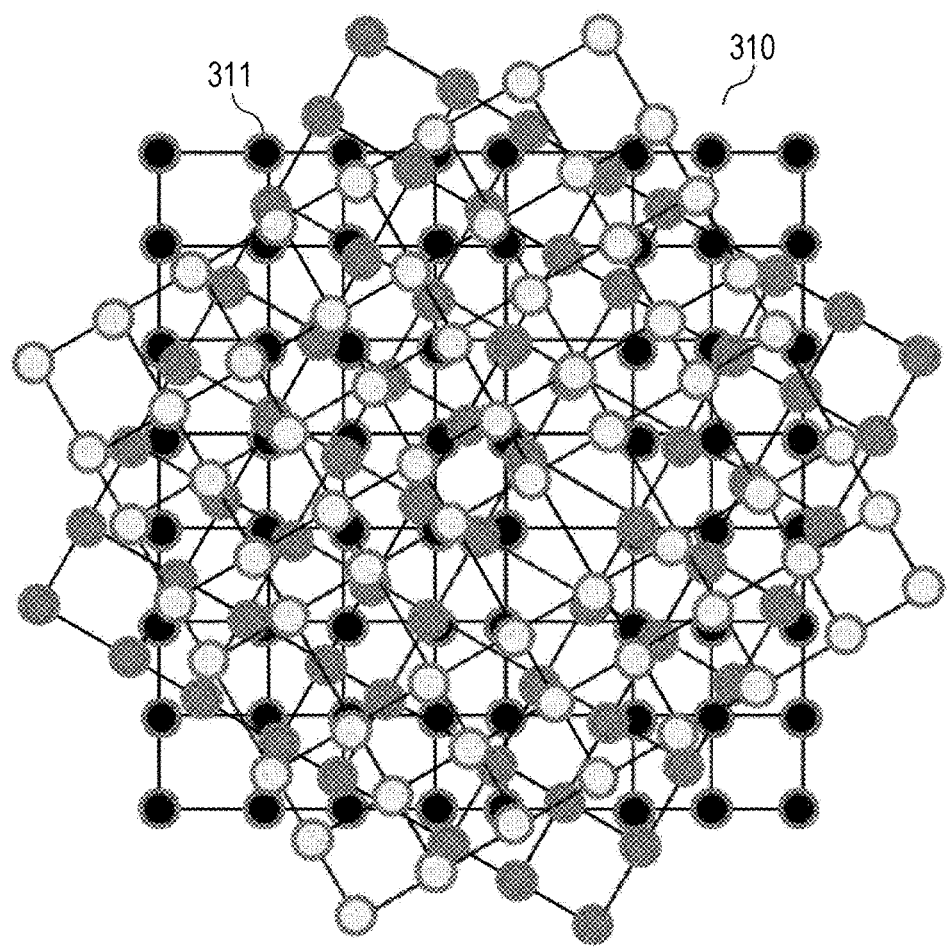
FIG. 8 shows an exemplary arrangement pattern of dots produced by a plurality of print operations according to the present exemplary embodiment.

FIG. 8 is a diagram showing an exemplary arrangement pattern of dots 311 when the pattern shown in FIG. 7 is printed three times while being rotated by 45° every time. Note that, the grid-like lines connecting dots 311 to each other are auxiliary lines and not printed lines.

As shown in FIG. 8, when a plurality of print operations are performed while thin film 300 is rotated, streak irregularities are hardly recognized. Such image 310 on thin film 300 of less noticeable streak irregularities easily blends with the skin.

Figure 9A:
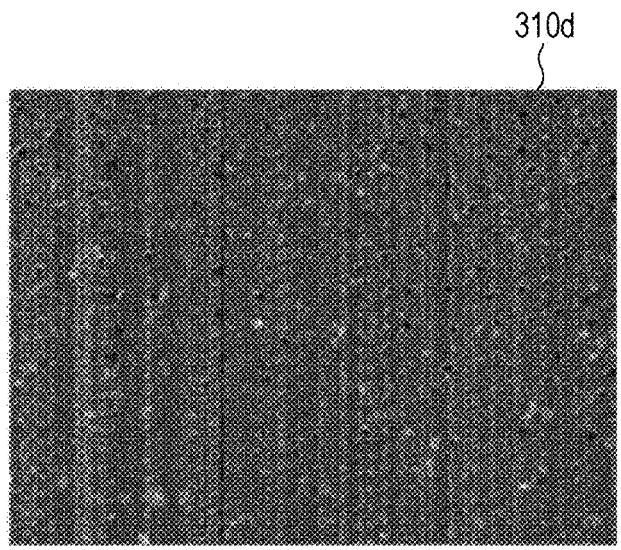
FIG. 9A shows an exemplary comparison of printed images between when the orientation of the thin film according to the present exemplary embodiment is changed and when not changed.
Figure 9B:
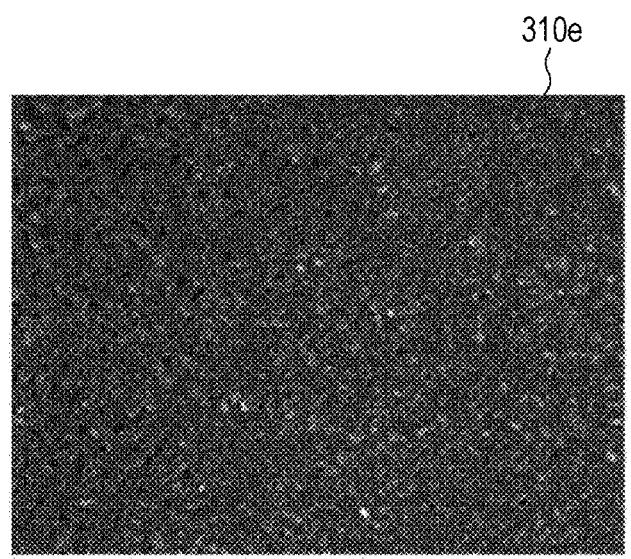
FIG. 9B shows an exemplary comparison of printed images between when the orientation of the thin film according to the present exemplary embodiment is changed and when not changed.

FIGS. 9A and 9B are diagrams showing an exemplary comparison of printed images between when a plurality of print operations are performed without changing the orientation of thin film 300 and when the orientation is changed.

When a plurality of print operations are performed without changing the orientation of thin film 300, as shown in FIG. 9A, streak irregularities extending in one direction (for example, Y-axis direction) is noticeable in image 310d. On the other hand, when a plurality of print operations are performed while the orientation of thin film 300 is changed, as shown in FIG. 9B, streak irregularities are not found in image 310e.

The rotation angle may be previously set to position switcher 530, or print controller 580 may control the rotation by position switcher 530 by an arbitrary angle. For example, when the print operation is performed for N times (N is an integer equal to 2 or more), position switcher 530 rotates thin-film carrier 510 by 180/N degrees. Note that, as described above, the rotation angle is desirably an angle determined based on diameter D and intervals dx, dy of dots 311 (droplets volume, gap, and print resolution), by which dots 311 do not overlap each other as much as possible.

<Operation of Apparatus>

Next, a description will be given of the operation of printing apparatus 100.

Figure 10:
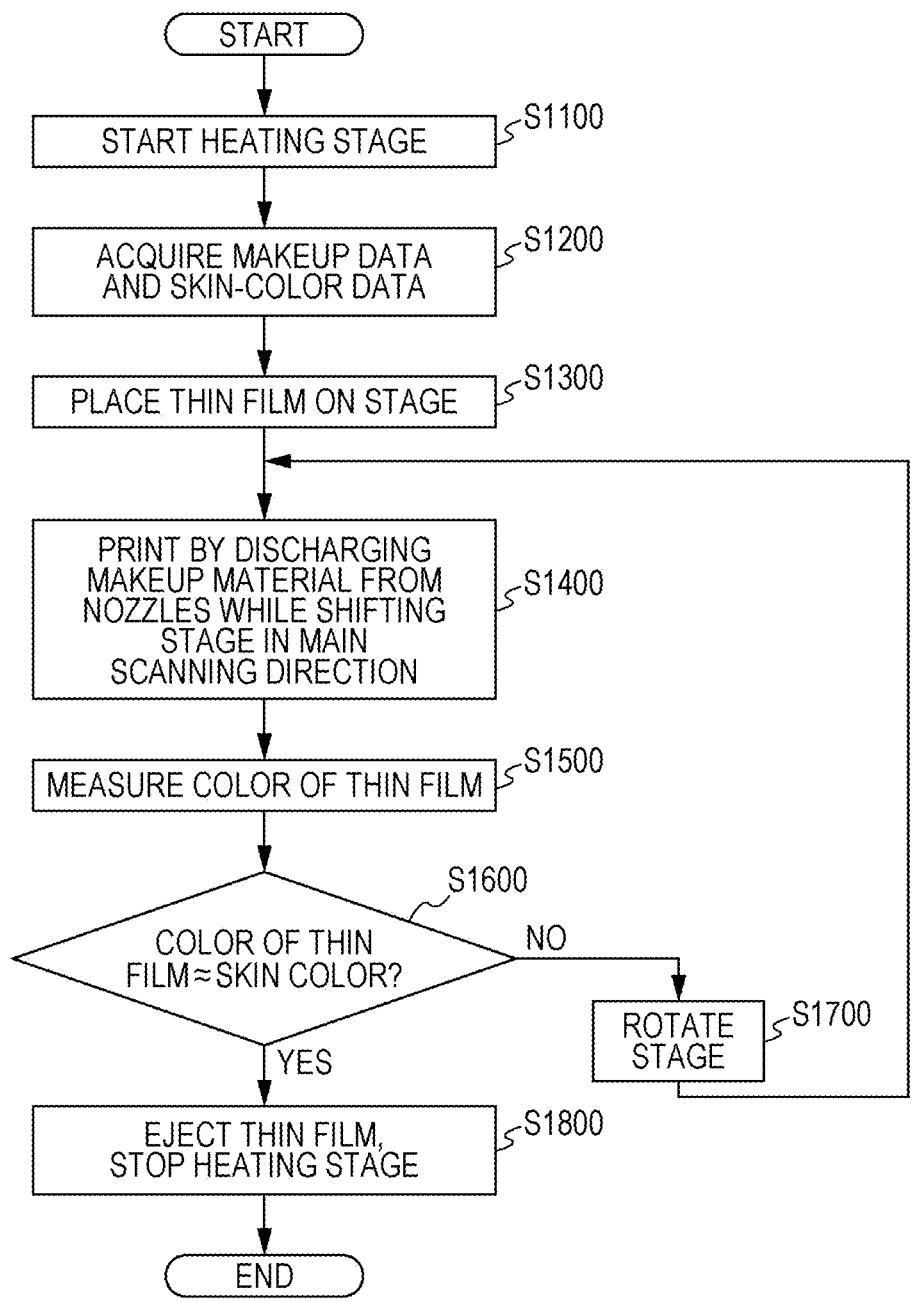
FIG. 10 is a flowchart showing exemplary operations of the printing apparatus according to the present exemplary embodiment.

FIG. 10 is a flowchart showing exemplary operations of printing apparatus 100. Printing apparatus 100 performs the following operations, for example in response to an instruction to manufacture a thin-film printed body from the makeup simulator apparatus described above. Such an operation is performed, for example, by print controller 580 controlling each of the constituent elements of printing apparatus 100.

In Step S1100, heater 520 starts to heat stage 10 (thin-film carrier 510).

In Step S1200, data acquirer 50 acquires makeup data and skin-color data.

In Step S1300, on stage 210 (thin-film carrier 510), thin film 300 is placed. Thin film 300 is placed on thin-film carrier 510 by the above-described thin-film supplier, for example.

In Step S1400, conveyer 540 shifts stage 210 (thin-film carrier 510) on which thin film 300 is placed in the main scanning direction (first direction 410, see FIG. 1). Then, droplet discharger 550 discharges the makeup material from the nozzles at the timing corresponding to the content of the makeup data when thin film 300 passes immediately below by the shifting operation, to thereby print the image represented by the makeup data.

Note that, on the premise that the print operation is performed for N times at an identical region of thin film 300, print controller 580 may control droplet discharger 550 such that the printed image concentration per print operation (that is, the discharge amount or discharge interval of the makeup material) becomes 1/N as great as the concentration of the completed image.

In Step S1500, conveyer 540 shifts stage 210 (thin-film carrier 510) such that thin film 300 is positioned immediately below print measurer 570. Then, print measurer 570 measures the color of thin film 300.

In Step S1600, print controller 580 determines whether or not the measured color of thin film 300 agrees with the skin color represented by the skin data. Such a determination is made by, for example, determining whether or not the distance in a prescribed color space is equal to or smaller than a prescribed threshold value.

Note that, when streak irregularities are noticeable, the area where the color of support body 610 is seen is great and therefore the measured color and the skin color are less likely to agree with each other. Accordingly, by determining whether or not the measured color agrees with the skin color represented by the skin data, whether or not the streak irregularities are sufficiently reduced can be determined.

When the color of thin film 300 does not agree with the skin color (S1600: NO), print controller 580 proceeds to Step S1700. Further, when the color of thin film 300 agrees with the skin color (S1600: YES), print controller 580 proceeds to Step S1800 which will be described later.

In Step S1700, position switcher 530 rotates stage 210 (thin-film carrier 510) on which thin film 300 is placed by the angle described above, and control returns to Step S1400. Note that, when the print operation is performed only in first direction 410, conveyer 540 returns stage 210 to the initial position (on the upstream side of droplet discharger 550).

As a result, thin film 300 is subjected to printing for a plurality of times in a plurality of different directions. Then, at the time point where the color of thin film 300 agrees with the skin color, control proceeds to Step S1800.

In Step S1800, printing apparatus 100 ejects the printed thin film 300 (the thin-film printed body) placed on stage 210 (thin-film carrier 510). Note that, such an ejection is performed by, for example, the thin-film ejector described above. Further, heater 520 stops heating stage 210 (thin-film carrier 510).

Through such operations, printing apparatus 100 can perform the print operation repeatedly for a plurality of times on thin film 300 while changing the orientation of thin film 300 relative to a plurality of nozzles until the color of thin film 300 agrees with the color of the user's skin.

Note that, heater 520 may constantly heat stage 210 irrespective of print timing. Alternatively, heater 520 may only perform heating after printing in Step S1400 has completed and until printing is started next time (for example, until the timing before color measurement in Step S1500 is started).

<Thin-Film Printed Body>

Here, a description will be given of the structure of the thin-film printed body having undergone printing for a plurality of times.

When it is desired to conceal spots of the skin or the like by makeup, it is effective to enhance the opacity and light reflectivity of the printed image. Accordingly, printing apparatus 100 uses, for example, a white-color makeup material exhibiting high reflectivity, to realize makeup which conceals spots or the like.

Figure 11A:
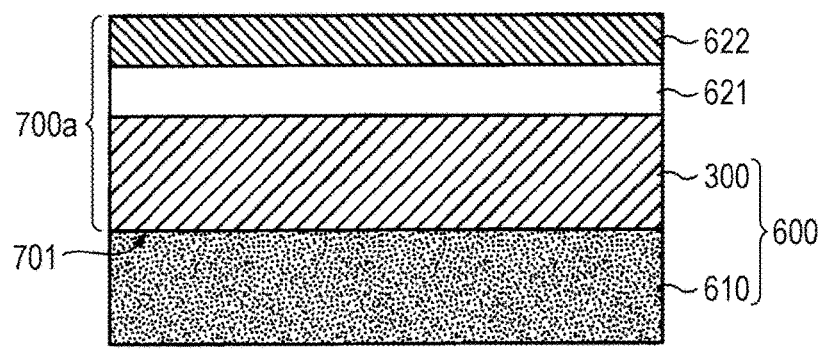
FIG. 11A is a cross-sectional view showing an exemplary structure of a thin-film printed body according to the present exemplary embodiment.
Figure 11B:
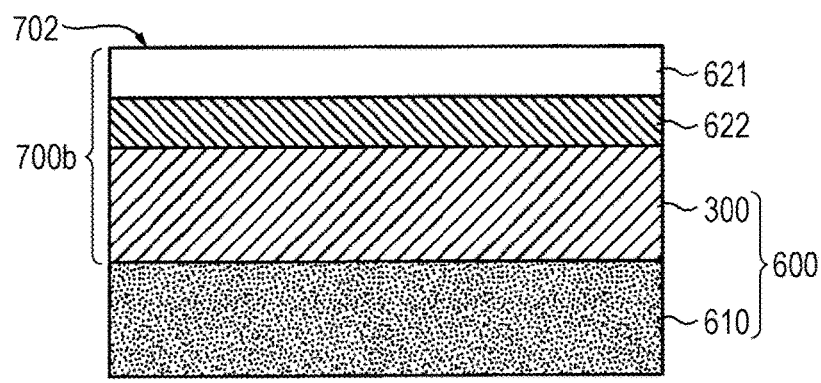
FIG. 11B is a cross-sectional view showing an exemplary structure of the thin-film printed body according to the present exemplary embodiment.
Figure 11C:
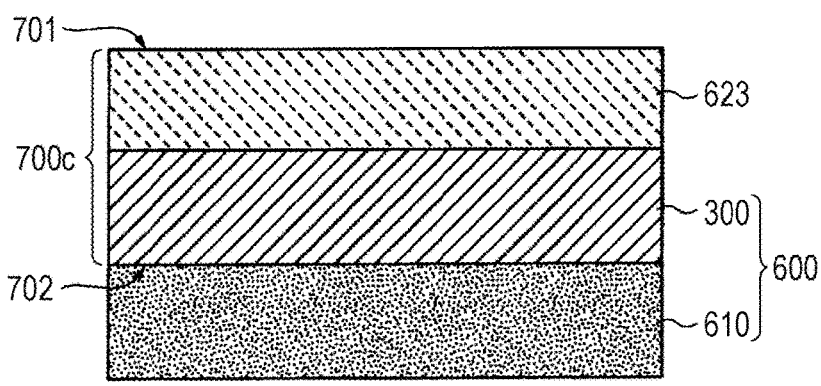
FIG. 11C is a cross-sectional view showing an exemplary structure of the thin-film printed body according to the present exemplary embodiment.

FIGS. 11A to 11C are each a cross-sectional view showing an exemplary structure of the thin-film printed body.

Printing apparatus 100 firstly forms, for example as shown in FIG. 11A, white-color layer 621 by printing a white-color makeup material for a plurality of times by the scheme described above on stack-layer body 600 made up of support body 610 and thin film 300. Then, printing apparatus 100 prints a skin-color makeup material for a plurality of times by the scheme described above on white-color layer 621, to form skin-color layer 622.

As a result, thin-film printed body 700a having thin film 300, white-color layer 621 formed on the surface of thin film 300, and skin-color layer 622 formed on the surface of white-color layer 621 is manufactured. White-color layer 621 functions as a concealing portion which conceals spots or the like. Further, skin-color layer 622 functions as a coloring portion which blends the color of thin-film printed body 700a with the skin color.

In this case, for example, the user peels off thin-film printed body 700a from support body 610, and affixes lower surface 701 having been tightly attached to support body 610 in thin-film printed body 700a onto the skin.

Alternatively, for example as shown in FIG. 11B, printing apparatus 100 forms skin-color layer 622 and white-color layer 621 on stack-layer body 600 in this order. As a result, thin-film printed body 700b having thin film 300, skin-color layer 622 formed on the surface of thin film 300, and white-color layer 621 formed on the surface of skin-color layer 622 is manufactured.

In this case, for example, the user peels off thin-film printed body 700b from support body 610, and affixes upper surface 702 provided with the print in thin-film printed body 700b onto the skin.

Further, for example as shown in FIG. 11C, printing apparatus 100 prints a makeup material of a mix-color of white and skin colors for a plurality of times by the scheme described above on stack-layer body 600, to form mixed-color layer 623. As a result, thin-film printed body 700c having thin film 300 and mixed-color layer 623 formed on the surface of thin film 300 is manufactured.

In this case, the user peels off thin-film printed body 700c from support body 610, and affixes lower surface 701 having been tightly attached to support body 610, or upper surface 702 provided with the print onto the skin.

In this manner, by printing a white-color makeup material exhibiting high reflectivity, the effect of concealing skin ground such as spots or wrinkles can be improved. Here, the above-described streak irregularities tend to be noticeable when such a makeup material exhibiting high light reflectivity is printed. In this term, since printing apparatus 100 is capable of effacing streak irregularities as described above, makeup which is natural and still exhibiting high concealing effect to spots or the like can be realized.

Note that, the color of the concealing portion concealing spots or the like may be color other than white, such as pale yellow which blends with skin color better, or pale violet which exhibits great concealing effect.

Effect of Present Exemplary Embodiment

As described above, with printing apparatus 100 according to the present exemplary embodiment, a makeup material is discharged from positions different from each other in the second direction while the thin film is shifted in the first direction, whereby printing on the thin film is performed. After the orientation of the thin film relative to the plurality of positions is changed, the thin film is again subjected to the printing.

Thus, printing apparatus 100 according to the present exemplary embodiment can realize more natural makeup in providing makeup using the thin-film printed body.

Variation of Present Exemplary Embodiment

Note that, the component and color of the makeup material, the material, color, structure and the like of the thin film and those of the support body are not limited to the example described above. For example, the color of the makeup material may be color corresponding to cosmetics such as cheek colors, other than skin color (for example, red or pink). Further, the makeup material may contain various functional components such as skincare components including a moisturizing component, a whitening component, a UV (Ultra Violet) cut component and the like.

For example, after printing apparatus 100 prints a skin-color makeup material on thin film 300, printing apparatus 100 further applies a skincare component. The user can simultaneously perform skincare and makeup by affixing the side of thin film 300 on which the skincare component is applied onto the skin.

Further, in the case where printing is to be performed on a region other than circular (for example, a lip-shaped region or the like), printing apparatus 100 may rotate the image represented by the print data by an angle identical to the rotation angle of thin-film carrier 510, and may discharge the makeup material based on the rotated image.

In contrast, printing apparatus 100 may repeat the operation of printing on a region other than circular (for example, a quadrangular region) while rotating thin-film carrier 510, without rotating the image represented by the print data. In this case, as the number of performing printing is greater, the printed image approximates a circle. The density of dots 311 at the center portion of the circular region is high, and becomes lower toward the outer edge.

Thus, printing apparatus 100 can easily produce a printed image in which the color is gradually faded from the center toward the outer edge, and more natural makeup suitable for cheek colors or the like can be realized.

Further, the angle and the number of rotation of thin-film carrier 510 are not limited to the example described above. Printing apparatus 100 may repeat print operations while changing the orientation of thin-film carrier 510 twice or four or more times, and may change the orientation of thin-film carrier 510 by an angle of a multiple of 90° or an angle exceeding 90°.

Further, instead of rotating thin-film carrier 510 while performing printing for a plurality of times, printing apparatus 100 may translate thin-film carrier 510. That is, printing apparatus 100 may perform printing for a plurality of times while changing the position of thin-film carrier 510.

In this case also, since the position of streak irregularities changes, streak irregularities can be effaced. In this case, position switcher 530 shifts the position of thin-film carrier 510 relative to conveyer 540, for example by a combination of a rail and a motor and the like. In the case where the direction of such translation is Y-axis direction, position switcher 530 can be implemented by using stage shifting mechanism 220 of conveyer 540, and a reduction in costs of the apparatus can be achieved.

Note that, printing apparatus 100 may perform both the rotation and translation of thin-film carrier 510. Further, printing apparatus 100 may rotate and/or translate thin-film carrier 510 in a different pattern every time printing is repeated, in the case where the printing is performed for three or more times on an identical region.

Further, a change in the position and/or orientation of thin-film carrier 510 may be made by a user's operation.

Still further, when the time taken for the makeup material printed on the thin film to fix is sufficiently short, printing apparatus 100 may not necessarily include heater 520.

Still further, in the case where it is based on the premise that the color and transparency of the image printed based on print data attain the desired color and transparency, printing apparatus 100 may not necessarily include print measurer 570. In this case, print controller 580 employs, for example, the number of times of performing printing as the criterion of determining whether or not to continue the printing.

Still further, the shift direction and rotation direction of the thin film, and the makeup material discharge direction of droplet discharger 550 are not limited to the example described above. For example, thin-film carrier 510 may vertically carry the thin film; conveyer 540 may shift the thin film in parallel to such a vertical plane; and droplet discharger 550 may discharge a makeup material in the horizontal direction toward the carried thin film. In this case, position switcher 530 must change the position and/or orientation of thin-film carrier 510 in the plane parallel to the vertical plane.

Still further, in addition to making a change in the position and/or orientation of thin-film carrier 510, printing apparatus 100 may make a change in the position and/or orientation of droplet discharger 550. Thus, it becomes possible to reduce the shift and/or rotation speed of droplet discharger 550 as compared to the conventional technique. Therefore, printing is stabilized as compared to the conventional technique, and it becomes possible to print an image in which streak irregularities are more suppressed.

Still further, the thin-film printed body manufactured by printing apparatus 100 can be used not only as cosmetics, but also in various fields such as special effects makeup and medication.

Still further, printing apparatus 100 may print droplets containing other various functional components described above such as lotion or medication, in place of a colored makeup material. In this case also, printing apparatus 100 can enhance the effect of the thin-film printed body on which droplets containing the functional components are printed. Note that, the makeup material described above can also be regarded as droplets containing a functional component of color.

Still further, the target to which the thin-film printed body manufactured by printing apparatus 100 is affixed is not limited to the skin and may be nails, teeth, eyes and the like. In this case, the skin-color data is desirably color data representing the color of the affix target. Note that, the data acquired by data acquirer 560 is not limited to the skin-color data, and may be data relating to the appearance of a human body such as the shape of the nose or nails, and data relating to the characteristics corresponding to the skin parts such as the sulci cutis density or the sweat gland density.

Still further, print measurer 570 may measure the print state of the thin film other than the color, such as an image obtained by capturing an image of the thin film, the reflectivity of light from the thin film and the like. In this case, print controller 580 may detect, for example, streak irregularities from the captured image, and determine whether or not to continue the printing based on the detection result.

Still further, in the structure of printing apparatus 100, for example, data acquirer 560 and print controller 580 may be disposed as being physically spaced apart from other constituent elements of printing apparatus 100. In this case, the spaced apart constituent elements each must include a communication circuit for communicating with each other.

<Summary of Present Disclosure>

A printing apparatus includes: a printer printing on a thin film by discharging, while shifting the thin film in a first direction, droplets containing a functional component from a plurality of positions differing from each other in a second direction; and a print uniformity controller that controls the printer to print such that position and/or orientation of the thin film is changed relative to the plurality of positions at each time of the printing.

Note that, in the printing apparatus, the printer may comprise: a thin-film carrier carrying the thin film; a conveyer shifting the thin-film carrier in the first direction; and a plurality of nozzles disposed at the plurality of positions and discharging the makeup material. The print uniformity controller may comprise: a position switcher switching position and/or orientation of the thin-film carrier relative to the conveyer; and a print controller performing the printing by using the printer before and after the switching.

Further, in the printing apparatus, the print controller may perform the printing on an identical range of the thin film before and after the switching.

Still further, in the printing apparatus, the print uniformity controller may have a heater heating the thin film.

Still further, in the printing apparatus, the position switcher may switch the position and/or orientation of the thin-film carrier in synchronization with an operation of the printer.

Still further, in the printing apparatus, the position switcher may switch the orientation of the thin-film carrier by rotating the thin-film carrier by an angle other than a multiple of 90 degrees.

Still further, in the printing apparatus, the position switcher may switch the orientation of the thin-film carrier in three or more orientations by rotating the thin-film carrier.

Still further, in the printing apparatus, the position switcher may switch the position of the thin-film carrier by shifting the thin-film carrier relative to the conveyer.

Still further, in the printing apparatus, the print uniformity controller may have a print measurer measuring a print state of the thin film, and the print controller may determine whether or not to continue the printing based on the measured print state.

Still further, in the printing apparatus, the droplets may be a colored makeup material.

Still further, in the printing apparatus, the print measurer may measure color of the thin film having undergone the printing, and the print controller may acquire color of a target to which the thin film is affixed, and may determine whether or not to continue the printing based on a comparison between the acquired color of the target and the measured color of the thin film.

The thin-film printed body of the present disclosure includes: a thin film having biocompatibility; a first makeup material layer made of a first-color makeup material formed on a surface of the thin film; and a second makeup material layer made of a second-color makeup material formed on a surface of the first makeup material layer.

Note that, in the thin-film printed body, the second makeup material layer is made up of a first plurality of droplets of the second-color makeup material arranged in a first direction, and a second plurality of droplets of the second-color makeup material arranged in a second direction.

Further, in the thin-film printed body, the first makeup material layer may be made of a plurality of droplets of the first-color makeup material arranged in a first direction, and the second makeup material layer may be made of a plurality of droplets of the second-color makeup material arranged in a second direction.

The method of manufacturing the thin-film printed body of the present disclosure includes: printing on a thin film by discharging, while shifting the thin film in a first direction, a makeup material from a plurality of positions differing from each other in a second direction; and changing position and/or orientation of the thin film relative to the plurality of positions at each time of the printing.

The printing apparatus, the thin-film printed body, and the method of manufacturing the thin-film printed body according to the present disclosure are useful as a printing apparatus, a thin-film printed body, and a method of manufacturing a thin-film printed body capable of enhancing the effect of the thin-film printed body.

What is claimed is:

1. A printing apparatus comprising:
   a printer printing on a thin film by discharging, while shifting the thin film in a first direction, droplets containing a functional component from a plurality of positions differing from each other in a second direction; and a print uniformity controller that repeatedly performs operations on the thin film a plurality of times, the operations including:
controlling the printer to print on the thin film; and
changing at least one of a position or an orientation of the thin film relative to the plurality of positions at each time of the plurality of times.

2. The printing apparatus according to claim 1, wherein the printer comprises:
   a thin-film carrier carrying the thin film;
   a conveyer shifting the thin-film carrier in the first direction; and
   a plurality of nozzles disposed at the plurality of positions and discharging the droplets, and wherein the print uniformity controller comprises:
      a position switcher switching the at least one of the position or the orientation of the thin-film carrier relative to the conveyer each time of the plurality of times; and
      a print controller controlling the printing by using the printer before and after the switching.

3. The printing apparatus according to claim 2, wherein the print controller performs the printing on an identical range of the thin film before and after the switching.

4. The printing apparatus according to claim 2, wherein the print uniformity controller includes a heater that heats the thin film.

5. The printing apparatus according to claim 2, wherein the position switcher switches the at least one of the position or the orientation of the thin-film carrier in synchronization with an operation of the printer.

6. The printing apparatus according to claim 5, wherein the position switcher switches the orientation of the thin-film carrier by rotating the thin-film carrier by an angle other than a multiple of 90 degrees.

7. The printing apparatus according to claim 5, wherein the position switcher switches the orientation of the thin-film carrier in three or more orientations by rotating the thin-film carrier.

8. The printing apparatus according to claim 5, wherein the position switcher switches the position of the thin-film carrier by shifting the thin-film carrier relative to the conveyer.

9. The printing apparatus according to claim 5, wherein
the print uniformity controller includes a print measurer that measures a print state of the thin film, and
the print controller determines whether or not to continue the printing based on the measured print state.

10. The printing apparatus according to claim 9, wherein the droplets are a colored makeup material.

11. The printing apparatus according to claim 10, wherein
the print measurer measures color of the thin film having undergone the printing, and
the print controller acquires color of a target to which the thin film is affixed, and determines whether or not to continue the printing based on a comparison between the acquired color of the target and the measured color of the thin film.

12. The printing apparatus according to claim 1, further comprising:
   a conveyor that returns the thin film to an initial position for each time of the plurality of times.

13. The printing apparatus according to claim 12, further comprising:
   a rotary table that changes the orientation of the thin film relative to the plurality of positions by changing the rotation angle of the thin film relative to the plurality of positions,
   wherein the initial position corresponds to the rotary table.

14. The printing apparatus according to claim 12,
wherein the thin film is rotated relative to the first direction while the thin film is returned to the initial position.

15. The printing apparatus according to claim 12,
wherein the printing on the thin film is performed only while shifting the thin film in the first direction.

16. The printing apparatus according to claim 1,
wherein the print uniformity controller is a processor.

* * * * *